(12) United States Patent
Cai et al.

(10) Patent No.: US 6,942,770 B2
(45) Date of Patent: *Sep. 13, 2005

(54) DISPOSABLE SUB-MICROLITER VOLUME BIOSENSOR WITH ENHANCED SAMPLE INLET

(75) Inventors: Xiaohua Cai, Needham, MA (US); Handani Winarta, Nashua, NH (US); Andy Vo, Somerville, MA (US); Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/126,818

(22) Filed: Apr. 19, 2002

(65) Prior Publication Data

US 2003/0196894 A1 Oct. 23, 2003

(51) Int. Cl.[7] ............................................. G01N 27/327
(52) U.S. Cl. ........................... 204/403.04; 204/403.14; 204/403.11
(58) Field of Search ........................ 204/403.01–403.15

(56) References Cited

U.S. PATENT DOCUMENTS

| | | |
|---|---|---|
| 4,897,173 A | 1/1990 | Nankai et al. |
| 5,120,420 A | 6/1992 | Nankai et al. |
| 5,232,856 A | 8/1993 | Firth |
| 5,264,103 A | 11/1993 | Yoshioka et al. |
| 5,266,179 A | 11/1993 | Nankai et al. |
| 5,288,636 A | 2/1994 | Pollmann et al. |
| 5,382,346 A | 1/1995 | Uenoyama et al. |
| 5,395,504 A | 3/1995 | Saurer et al. |
| 5,437,999 A | 8/1995 | Diebold et al. |
| 5,496,453 A | 3/1996 | Uenoyama et al. |
| 5,508,171 A | 4/1996 | Walling et al. |

(Continued)

FOREIGN PATENT DOCUMENTS

EP         1152239 A1 * 11/2001   ......... G01N/27/327

OTHER PUBLICATIONS

CAPLUS abstract of Joo et al. ("A biosensor stabilized by polyethylene glycol for the monitoring of hydrogen peroxide in organi solvent media," Enzyme and Microbial. technology (1996), 19(1), 50–56).*
CAPLUS abstract of Saby et al. ("Glucose sensor based on carbon paste elecrode incorporating poly(ethylene glycol)–modified glucose oxidase and various mediators," Analytica Chimica 91995), 304(10, 33–9).*
CAPLUS abstract of Mizutani et al. ("Amperometric glucose–sensor electrode based on carbon paste containing poly(ethylene glycol)–modified oxidase and cobalt octaethoxyphthalocyanine," Analytica Chimica (1995), 300(1–3), 59–64.*
CAPLUS abstract of Yao et al. (Preparation of a carbon paste/alcohol dehydrogenase electrode based on oil–soluble mediator Chemical Sensors (1998), 14(Suppl. A, Proceedings of the 26th Chemcial Sensor Symposium, 1998), 153–156).*
Sigma–Aldrich catalog description for Triton X–100 downloaded from the Sigma–Aldrich website on Jun. 18, 2004.*

*Primary Examiner*—Alex Noguerola
(74) *Attorney, Agent, or Firm*—Robert R. Deleault, Esq.; Mesmer & Deleault, PLLC

(57) ABSTRACT

A disposable electrode strip for testing a fluid sample including a laminated strip with a first and second end, a vent, an open path for receiving a fluid sample of less than one microliter beginning from the first end and connecting to the vent, a working electrode, a reference electrode and a pseudo-working electrode embedded in the laminated strip within the open path and proximate to the first end, a reagent matrix coextensive within the open path and covering the three electrodes, and conductive contacts located at the second end of the laminated strip.

47 Claims, 5 Drawing Sheets

U.S. PATENT DOCUMENTS

| | | |
|---|---|---|
| 5,563,067 A | 10/1996 | Sugihara et al. |
| 5,628,890 A | 5/1997 | Carter et al. |
| 5,670,031 A | 9/1997 | Hintsche et al. |
| 5,682,884 A | 11/1997 | Hill et al. |
| 5,708,247 A | 1/1998 | McAleer et al. |
| 5,755,953 A | 5/1998 | Henning et al. |
| 5,759,364 A | 6/1998 | Charlton et al. |
| 5,762,770 A | 6/1998 | Pritchard et al. |
| 6,004,441 A | 12/1999 | Fujiwara et al. |
| 6,258,229 B1 | 7/2001 | Winarta et al. |
| 6,287,451 B1 * | 9/2001 | Winarta et al. ........... 205/777.5 |
| 6,299,757 B1 * | 10/2001 | Feldman et al. ............. 205/775 |
| 6,582,573 B2 * | 6/2003 | Douglas et al. ........... 204/403.1 |

* cited by examiner

DISPOSABLE SUB-MICROLITER VOLUME BIOSENSOR WITH ENHANCED SAMPLE INLET

BACKGROUND OF THE INVENTION

1. Field of the Invention

The present invention relates generally to electrochemical sensors that can be used for the quantification of a specific component or analyte in a liquid sample. Particularly, this invention relates to a new and improved electrochemical sensor and to a new and improved method of fabricating electrochemical sensors. More particularly, this invention relates to a disposable electrochemical sensor that is inexpensive to manufacture. Even more particularly, this invention relates to a disposable electrochemical sensor that gives accurate readings and requires only about 0.2 microliter of fluid sample. Still even more particularly, this invention relates to disposable electrochemical sensors which are used for performing electrochemical assays for the accurate determination of analytes in physiological fluids.

2. Description of the Prior Art

Biosensors have been used in the determination of concentrations of various analytes in fluids for more than three decades. Of particular interest is the measurement of blood glucose. It is well known that the concentration of blood glucose is extremely important for maintaining homeostasis. Products that measure fluctuations in a person's blood sugar, or glucose levels, have become everyday necessities for many of the nation's millions of diabetics. Because this disorder can cause dangerous anomalies in blood chemistry and is believed to be a contributor to vision loss and kidney failure, most diabetics need to test themselves periodically and adjust their glucose level accordingly, usually with insulin injections. If the concentration of blood glucose is below the normal range, patients can suffer from unconsciousness and lowered blood pressure which may even result in death. If the fasting blood glucose concentration is higher than the normal range, this can result in vision loss, kidney failure and vascular diseases. Thus, the measurement of blood glucose levels has become a daily necessity for diabetic individuals who control their level of blood glucose by insulin therapy.

Patients who are insulin dependent are instructed by doctors to check their blood-sugar levels as often as four times a day. To accommodate a normal life style to the need of frequent monitoring of glucose levels, home blood glucose testing was made available with the development of reagent strips for whole blood testing.

One type of blood glucose biosensors is an enzyme electrode combined with a mediator compound which shuttles electrons between the enzyme and the electrode resulting in a measurable current signal when glucose is present. The most commonly used mediators are potassium ferricyanide, ferrocene and its derivatives, as well as other metal-complexes. Many sensors based on this second type of electrode have been disclosed.

However, many of the prior art devices require a test sample volume of greater than 2 microliters. This volume of test sample can only be obtained from a patient, for example, using a needle and syringe, or by lancing a portion of the skin such as the fingertip and "milking" the area to obtain a useful sample volume. These procedures are inconvenient for the patient, and often painful, particularly when frequent samples are required. Less painful methods for obtaining a sample are known such as lancing the arm or thigh, which have a lower nerve ending density. However, lancing the body in the arm or thigh typically produces submicroliter sample volumes of blood because these areas are not heavily supplied with near-surface capillary blood vessels. Because the present invention requires as little as 0.2 microliters of blood, it allows not only sampling from the finger tip with much less pain, but also a possibility to obtain adequate blood samples from alternate sites.

Additional shortcomings of the prior art devices are that they have a more limited linear range, usually up to about 600 mg/dL. Further, they require a relatively longer waiting time before a reading can be achieved. Another shortcoming of the biosensor having an end or side inlet for direct introduction of the blood sample to the sample chamber from the source of the blood droplet is the inadvertent blockage or partial blockage of the inlet by the blood source. Users tend to push the biosensor hard against the blood sampling point such as at the finger or the arm. Because the entrance to the capillary channel of the biosensor is small, such action typically blocks or partially blocks the inlet. The result is that (1) the blood does not enter the capillary channel at all, or (2) the blood partially enters the channel but does not fill it up sufficiently, or (3) the blood fills up the capillary channel very slowly. Under scenario (1), the meter may not be triggered and thus not reading is made. Under scenarios (2) and (3), the meter may not be triggered or it may be triggered but gives inaccurate test results due to insufficient sample or the slowness of the capillary filling action.

Because of the importance of obtaining accurate glucose readings, it would be highly desirable to develop a reliable and user-friendly biosensor strips that do not have all of the shortcomings mentioned above.

Therefore, what is needed is an electrochemical sensor which requires less sample volume than previously required by the prior art. What is further needed is an electrochemical sensor which has a wide linear measurement range; that is, a sensor useable over a wider glucose concentration. What is still further needed is an electrochemical sensor which has a relatively short wait time for development of a steady-state response. What is also needed is an electrochemical sensor with a modified inlet port to facilitate introduction of the sample into the sample chamber of the electrochemical sensor.

SUMMARY OF THE INVENTION

It is an object of the present invention to provide an improved electrochemical sensor which combines an enzyme and a mediator. It is a further object of the present invention to provide an electrochemical sensor which requires less sample volume than previously required by the prior art. It is still another object of the present invention to provide an electrochemical sensor which can measure a small volume of sample without the use of a mesh layer in the sample path. It is yet another object of the present invention to provide an electrochemical sensor which has a wide linear measurement range and a relatively short wait time for development of a steady-state response. It is another object of the present invention to provide an electrochemical sensor that has a modified inlet port to facilitate sample introduction.

The present invention achieves these and other objectives by providing an electrochemical sensor which requires a sample size of only about 0.2 microliters and does not use a mesh layer in the sample path as a means of achieving a reduced size of the sample. Further the present invention uses a reagent composition which allows readings, which correlate very closely to the analyte concentration in the fluid sample, to be taken 5 seconds after the fluid sample enters the sample channel.

The present invention has a laminated, elongated body having a sample fluid channel connected between an opening on one end of the laminated body and a vent hole spaced from the opening. The sample fluid channel is sized to optimize the quick flow of a sample such as whole blood into the channel. Within the fluid channel lies at least one working electrode and a reference electrode, preferably a working electrode, a reference electrode and a pseudo-working electrode. The arrangement of the working electrode and the reference electrode is not important for purposes of the results obtained from the electrochemical sensor. The working electrode, the reference electrode and the pseudo-working electrode are each in electrical contact with separate conductive conduits, respectively. The separate conductive conduits terminate and are exposed for making an electrical connection to a reading device on the end opposite the open channel end of the laminated body.

The laminated body has a base insulating layer made from a plastic material. The base insulating layer has a conductive layer on one side. The conductive layer may be deposited on the insulating layer by screen printing, by vapor deposition, or by any method that provides for a conductive layer which adheres to the base insulating layer and substantially covers all of the base insulating layer. The vapor-deposited conductive layer is separated into conductive conduits by etching/scribing the conductive layer. The etching process may be accomplished chemically, by mechanically scribing lines in the conductive layer, by using a laser to scribe the conductive layer into separate conductive conduits, or by any means that will cause a break between and among the separate conductive conduits required by the present invention. The preferred conductive coatings are gold film or a tin oxide/gold film composition/layer.

It should be pointed out that the gold film or tin oxide/gold film itself cannot function as a reference electrode. To make the reference electrode work, there must be a redox reaction (e.g., $Fe(CN)_6^{3-}+e^-\rightarrow Fe(CN)_6^{4-}$) at the electrically conducting material when a potential is applied. Therefore, a redox couple or mediator must be present at the conducting material used for the reference electrode.

The unique feature of the present invention is its ability to measure sample sizes as small as 0.10 microliters, or smaller, without using opposing working and reference electrodes and a sorbent/mesh layer therebetween to reduce the required sample volume for measurement. This is is achieved by reducing the width and length of the U-shaped cutout and by using a thinner middle layer.

The laminated body also has a middle insulating layer on top of the base layer. The middle layer is also made of a plastic insulating material and creates the sample fluid channel of the laminated body. It contains a U-shaped cutout on one end which overlays the electrode portion of the conductive conduits on the base layer with the open end corresponding to the open end of the laminated body described earlier.

The middle layer must be of sufficient thickness for loading a sufficient amount of chemical reagent for use as an electrochemical sensor while maintaining a flow-channel dimension having optimum blood flow characteristics. The U-shaped cutout contains chemical reagent. The chemical reagent has a redox mediator with at least one of a stabilizer, a binder, a surfactant, a buffer, and an enzyme capable of catalyzing a reaction involving a substrate for the enzyme. The redox mediator is capable of transferring electrons between the enzyme-catalyzed reaction and the working electrode. It also makes the reference electrode function.

The laminated body of the present invention has a top layer with a vent opening and an inlet notch. The vent opening is located such that at least a portion of the vent opening overlays the bottom of the U-shaped cutout exposing a portion of the chemical reagent of the middle insulating layer. The vent allows air within the sample fluid channel to escape as the sample fluid enters the open end of the laminated body. The inlet notch facilitates sample introduction through the inlet by creating a top inlet aperture, which is in communication with the end of the inlet of the sensor. In the event that the sample inlet port is inadvertently blocked by the source of the blood sample such as a finger, the inlet notch remains open for receiving the sample fluid.

The sample fluid generally fills the sample fluid channel by capillary action. In small volume situations, the extent of capillary action is dependent on the hydrophobic/hydrophilic nature of the surfaces in contact with the fluid undergoing capillary action. This is also known as the wetability of the material. Capillary forces are enhanced by either using a hydrophilic insulating material to form the top layer, or by coating at least a portion of one side of a hydrophobic insulating material with a hydrophilic substance in the area of the top layer that faces the sample fluid channel between the open end of the laminated body and the vent opening of the top layer. It should be understood that an entire side of the top layer may be coated with the hydrophilic substance and then bonded to the second middle layer.

The electrode portions, located within the sample fluid channel, contain reagent material for the working electrode (W), the reference electrode (R) and the pseudo-working electrode ($W_0$). A reagent mix is disposed into the fluid channel thus covering the electrode portions of the base insulating layer and the conductive conduits. A sufficient amount of reagent mix is deposited within the U-shaped cutout of the middle insulating layer to substantially cover all of the conductive surface delineated by the U-shaped cutout. The amount of the reagent mix used is such that the reagent matrix created upon drying is sufficient for use as an electrochemical sensor yet provides enough empty space above the reagent matrix to allow rapid blood flow through the fluid channel. The reagent matrix has a redox mediator with at least one of a stabilizer, a binder, a surfactant, a buffer, and an enzyme capable of catalyzing a reaction involving a substrate for the enzyme.

The possible electrode arrangements within the sample fluid channel may be $W$-$R$-$W_0$, $W$-$W_0$-$R$, $R$-$W$-$W_0$, $R$-$W_0$-$W$, $W_0$-$W$-$R$ or $W_0$-$R$-$W$ with the arrangement listed as the arrangement of electrodes would appear from the open end of the laminated body to the vent opening. The preferred position was found to be $W$-$R$-$W_0$; that is, as the sample fluid entered the open end of the laminated body, the fluid would cover W first, then R, then $W_0$.

The pseudo-working electrode, $W_0$, is positioned so that the sample fluid reaches it last. The resulting current at $W_0$ thus triggers the reading meter to start the measurement and analyte concentration determination process. Such an arrangement obviates reliability and accuracy problems due to an insufficient sample fluid size. It should be pointed out that $W_0$ can also be used as a counter electrode. The resulting three-electrode system (i.e. working electrode, reference electrode and counter electrode) would be used in the case of a sample fluid having a large IR drop. It should also be pointed out that impedance between any two electrodes could be used to estimate the hematocrit of a blood sample and therefore to correct the hematocrit interference.

All of the advantages of the present invention will be made clearer upon review of the detailed description, drawings and appended claims.

DETAILED DESCRIPTION OF THE PREFERRED EMBODIMENT

Figure 1:
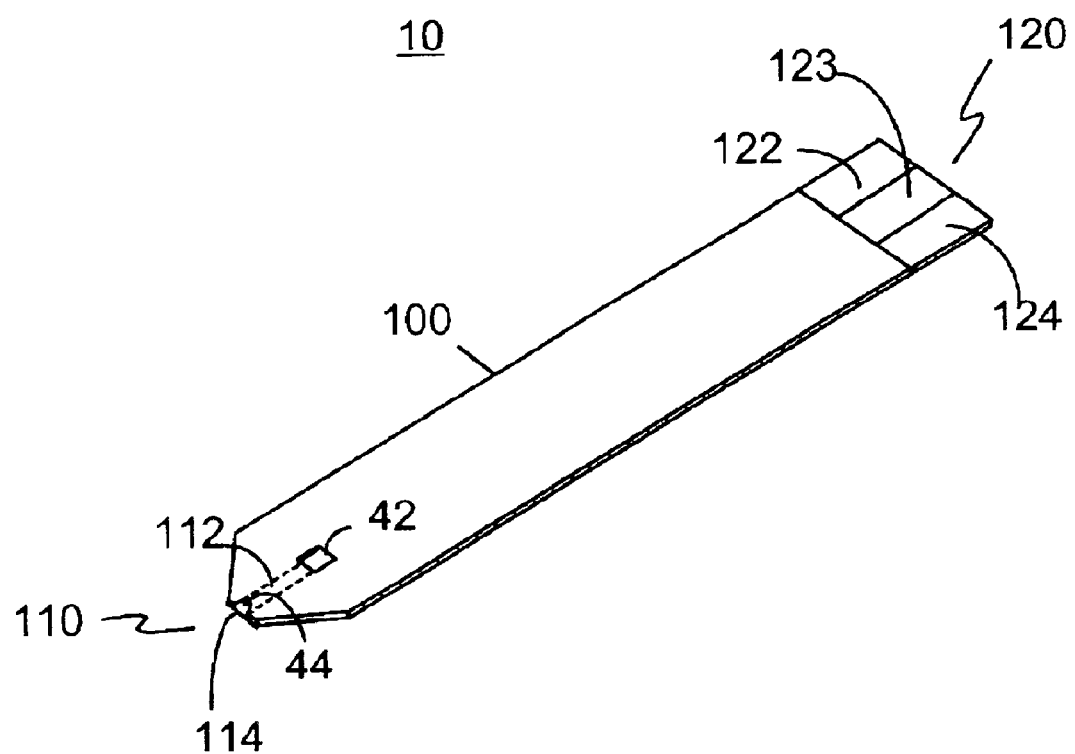
FIG. 1 is a perspective view of the present invention showing the open end, the vent and the electrical contact points of the laminated body.

The preferred embodiment of the present invention is illustrated in FIGS. 1–4. FIG. 1 shows a sensor 10 of the present invention. Sensor 10 has a laminated body 100, a fluid sampling end 110, an electrical contact end 120, and a vent opening 42. Fluid sampling end 110 includes a sample fluid channel 112 between a sampling end aperture 114 and vent opening 42. Sampling end 110 also includes an inlet notch 44. Electrical contact end 120 has three discreet conductive contacts 122,123 and 124.

Figure 2:
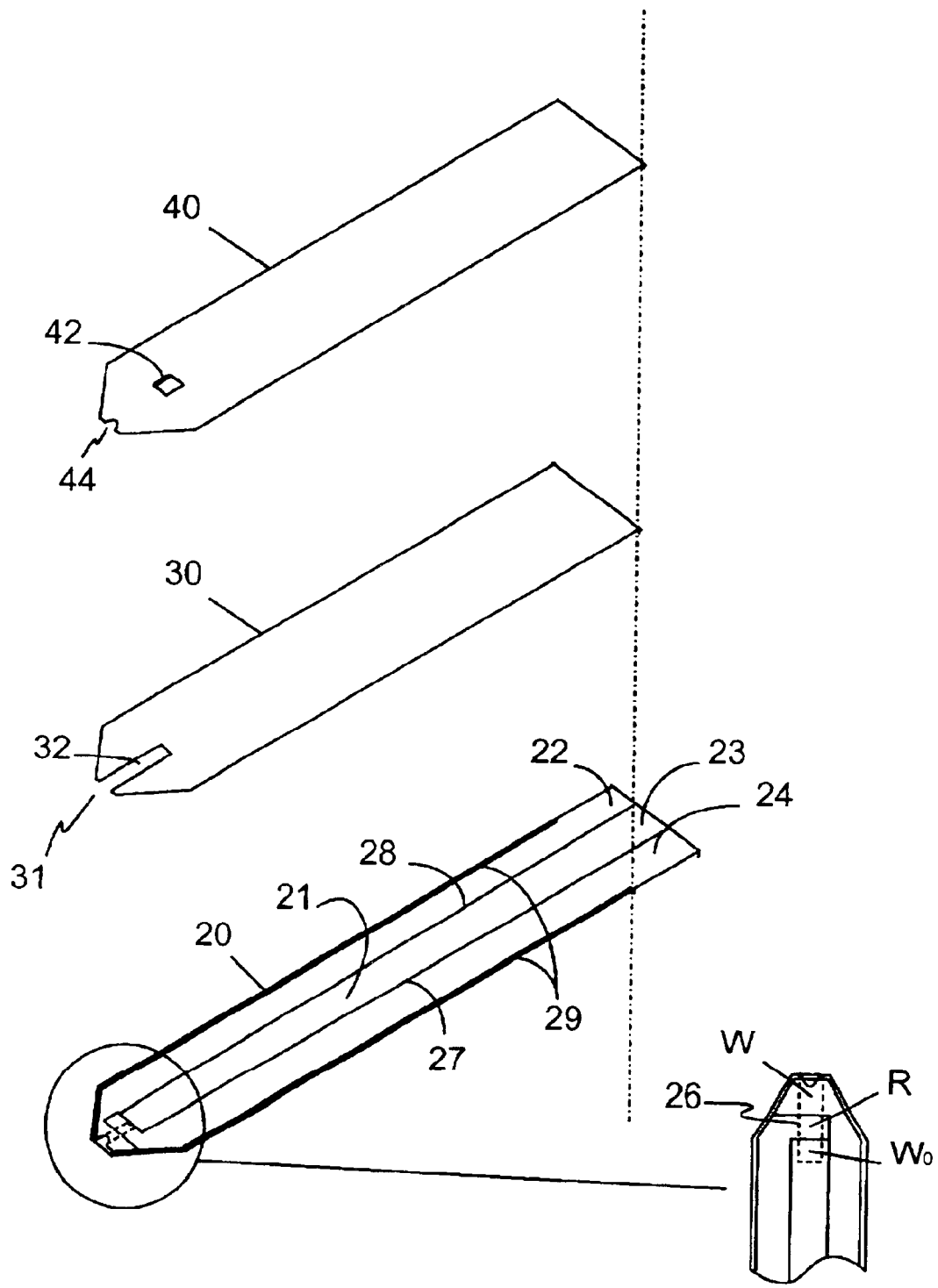
FIG. 2 is an exploded, perspective view of the present invention showing the various layers of the laminated body.

Referring now to FIG. 2, laminated body 100 is composed of a base insulating layer 20, a middle layer 30, and a top layer 40. All layers are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, acrylic and polystyrene. Base insulating layer 20 has a conductive layer 21 on which is delineated a first conductive conduit 22, a second conductive conduit 23 and a third conductive conduit 24. Conductive conduits 22, 23 and 24 may be formed by scribing or scoring the conductive layer 21 as illustrated in FIG. 2 and shown as scribe line 27 and 28 or by silk-screening the conductive conduits 22, 23 and 24 onto base layer 20. Scribing or scoring of conductive layer 21 may be done by mechanically scribing the conductive layer 21 sufficiently to create the three independent conductive conduits 22, 23 and 24. The preferred scribing or scoring method of the present invention is done by using a carbon dioxide ($CO_2$) laser, a YAG laser or an eximer laser. An additional scoring line 29 (enlarged and not to scale; for illustrative purposes only) may be made, but is not necessary to the functionality of sensor 10, along the outer edge of base layer 20 in order to avoid potential static problems which could give rise to a noisy signal. Conductive layer 21 may be made of any electrically conductive material, preferably gold or tin oxide/gold. A useable material for base layer 20 is a tin oxide/gold polyester film (Cat. No. FM-1) or a gold polyester film (Cat. No. FM-2) sold by Courtaulds Performance Films, Canoga Park, Calif.

Middle layer 30 has a U-shaped channel cutout 32 located at middle layer sensor end 31. The U-shaped cutout can be made by using a laser or diecut. The length of channel cutout 32 is such that when middle layer 30 is layered on top of base layer 20, electrode areas W, R and $W_0$ are within the space defined by channel cutout 32. The thickness of middle layer 30 was found to be critical for the volume of the capillary channel and for the speed of the sample fluid flow into sample fluid channel 112, which is filled by capillary action of the sample fluid. Channel cutout 32 holds the reagent matrix 50, more clearly shown in FIG. 3, forming the working electrode, the reference electrode and the pseudo-working electrode. Typically, the reagent matrix 50 must be loaded with a redox mediator to make the reference electrode function. If R is not loaded with a redox reagent or mediator, working electrode W and $W_0$ will not work. Electrode areas W, $W_0$ and R are loaded preferably with the same chemical reagent. The reagents preferably contain an oxidized form of a redox mediator, a stabilizer, a binder, a surfactant, a buffer, and an enzyme. Typically, the redox mediator may be at least one of ferrocene, potassium ferricyanide, other ferrocene derivatives, or other organic and inorganic redox mediators. The preferred stabilizer is polyethylene glycol, the preferred binder is methyl cellulose, the preferred surfactant is t-octylphenoxypolyethoxyethanol, and the preferred buffer is a citrate buffer. The enzyme is capable of catalyzing a reaction involving a substrate for the enzyme or a substrate catalytically reactive with an enzyme and a mediator capable of transferring electrons transferred between the enzyme-catalyzed reaction and the working electrode to create a current representative of the activity of the enzyme or substrate and representative of the compound. The enzyme could be glucose oxidase, lactate oxidase, cholesterol oxidase and creatinine amidohydrolase.

Top layer 40, which is placed over and coextensive with middle layer 30, has a vent opening 42 spaced from fluid sample end 110 of sensor 10 to insure that sample fluid in fluid channel 112 will completely cover electrode areas W, R and $W_0$. Vent opening 42 is placed in top layer 40 so that it will align somewhat with the bottom of channel cutout 32 of middle layer 30, the bottom meaning the channel cutout 32 located furthest from sensor end 31. Preferably, vent opening 42 will expose a portion of and partially overlay the bottom of the U-shaped cutout 32 of middle layer 30.

Top layer 40 also includes an inlet notch 44 at fluid sample end 110 of sensor 10. Inlet notch 44 is included to facilitate sample loading in fluid channel 112 where sampling end aperture 114 could be inadvertently blocked thus preventing the sample fluid from entering fluid channel 112 if sample notch 44 were absent. Sample notch 44 may have any shape and is not limited to the semi-circular shape shown. The vent opening and the inlet notch can be made by using a laser or by diecut.

Figure 3:
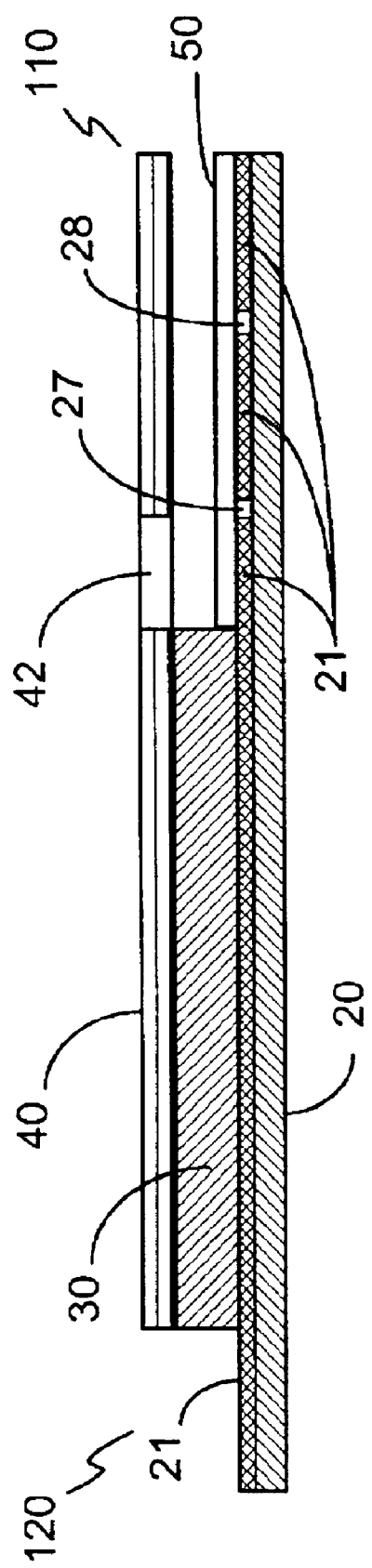
FIG. 3 is a cross-sectional view of the present invention of FIG. 1
Figure 4:
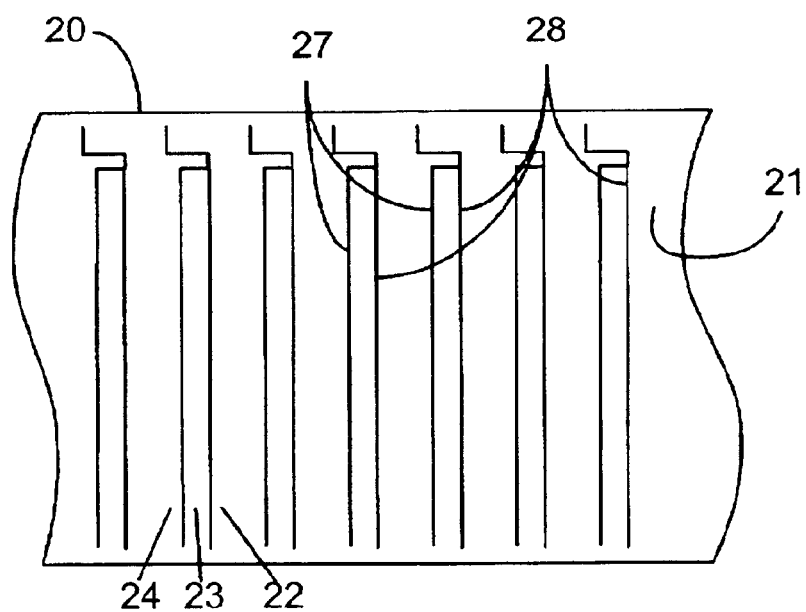
FIGS. 4A, 4B and 4C are top views of a segment of a strip of each layer of the present invention showing the patterns for making multiple sensors of the present invention.
FIG. 4D is a top view of a segment of the laminated strip of the present invention showing the patterns for making multiple sensors of the present invention.
Figure 4:
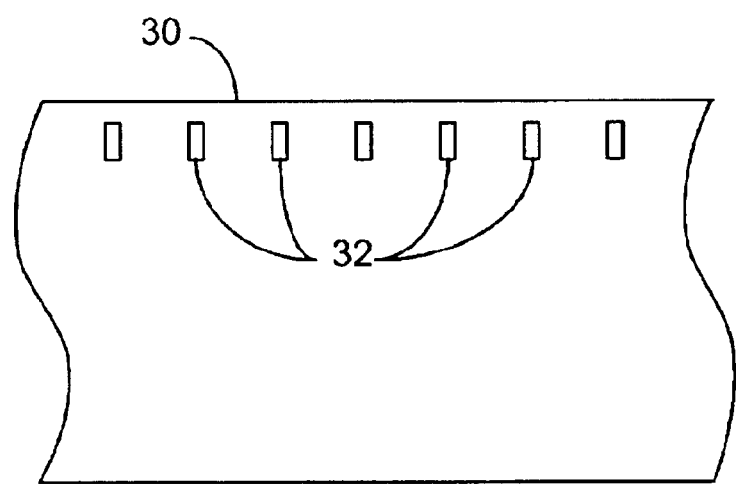
Figure 4:
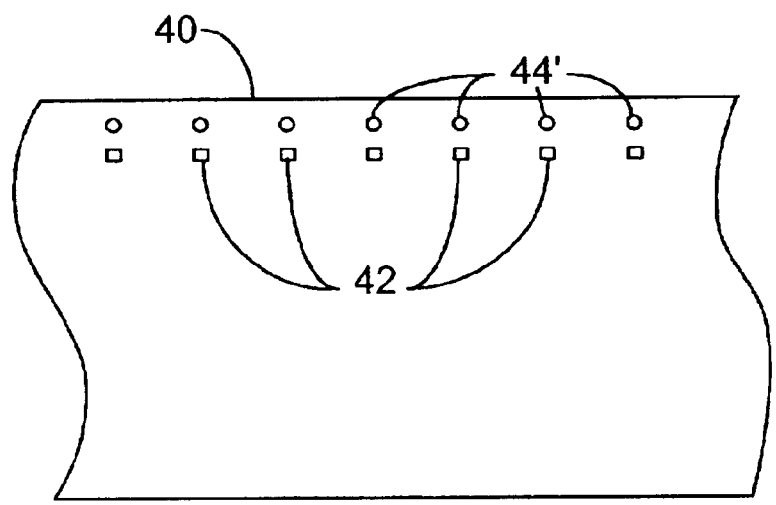
Figure 4:
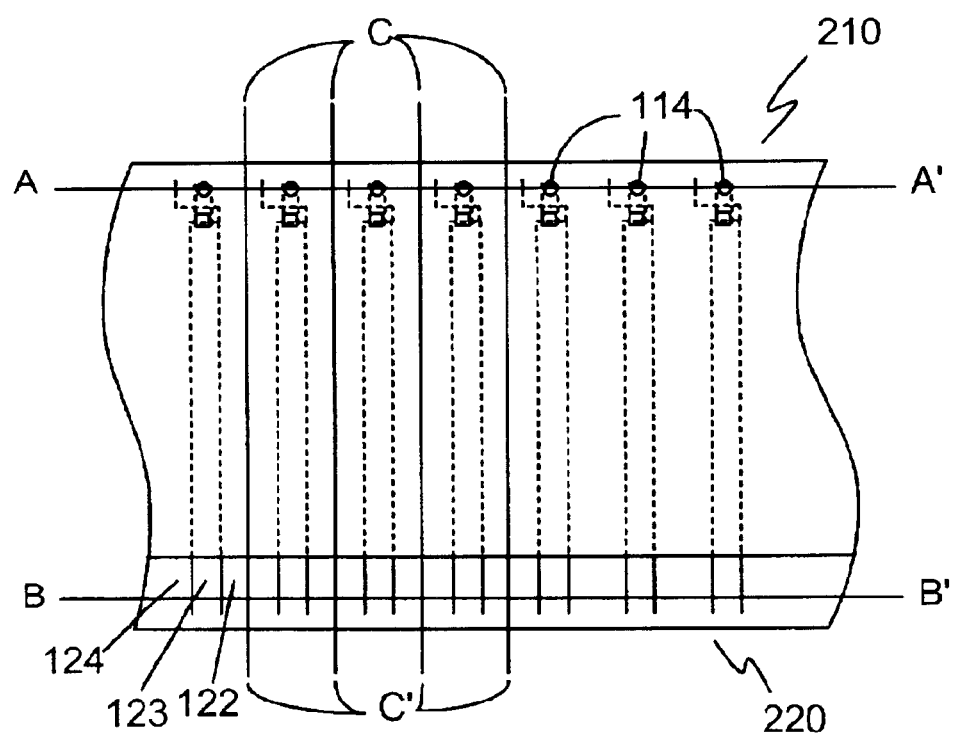

FIG. 3 shows an enlarged cross-sectional view of the various layers of the present invention. The layers are not to scale in order that the relationship of each component of the present invention may be better understood by those skilled in the art, especially scribe lines 27 and 28.

Preparation of Electrode Reagent Matrix

The electrode reagent matrix comprises the oxidized form of a redox mediator, a stabilizer, a binder, a surfactant, a buffer, and an enzyme. The oxidized form of the redox mediator, potassium ferricyanide, was found to be stable in the matrix. Suitable potassium ferricyanide is available from Sigma Chemical, St. Louis, Mo. (Cat. No P3667). The quantity used in the formulation must be sufficient to attain a workable linear range. The enzyme must also have sufficient activity, purity and stability. A commercially available glucose oxidase may be obtained from Biozyme, San Diego, Calif. as Cat. No. G03A, about 270 U/mg. The stabilizer must be sufficiently water-soluble and be capable of stabilizing both the mediator and the enzyme. The preferred stabilizer is polyethylene glycol (Cat. No. P4338, Sigma Chemicals, St. Louis, Mo.). The binder should be capable of binding all other chemicals in the reagent matrix in electrode areas W, R and $W_0$ to the conductive surface/layer 21 of base layer 20. The preferred binder is Methocel 60 HG (Cat. No. 64655, Fluka Chemical, Milwaukee, Wis.). The buffer solution must have sufficient buffer capacity and pH value to optimize the enzyme reaction. A 0.05M citrate buffer is preferred. Citric acid and sodium citrate used in making the citrate buffer may be obtained from Sigma Chemical. The surfactant is necessary to facilitate dispensing of the electrode reaction matrix into channel cutout 32 as well as for quickly dissolving the dry chemical reagents involved in forming the reagent matrix. The amount and type of surfactant is selected to assure the previously mentioned functions and to avoid a denaturing effect on the enzyme. The preferred surfactant is Triton X-100 available from Fluka Chemical, Milwaukee, Wis. (Cat. No. 94443). The reagent matrix is obtained by preparing a reagent mix as follows:

Step 1: Prepare 50 mM citrate buffer (pH 5.7) by dissolving 0.1512 grams citric acid and 1.2580 grams sodium citrate in 100 ml of deionized water.

Step 2: Prepare a 1% methocel 60 HG solution by stirring 1 gram of methocel in 100 ml of citrate buffer from Step 1 for 12 hours.

Step 3: Add 0.3 ml of 10% Triton X-100 into the methocel solution.

Step 4: Add 2.5 grams of polyethylene glycol into the solution from Step 3.

Step 5: While stirring, add 6.5 grams potassium ferricyanide to the solution of Step 4.

Step 6: Add 1.0 gram of glucose oxidase to the solution of Step 5 and stir for 10 minutes or until all solid materials are completely dissolved.

Electrode Construction

A piece of a gold or tin oxide/gold polyester film available from Courtaulds FOR Performance Films is cut to shape, as illustrated in FIG. 2, forming base layer 20 of sensor 10. A $CO_2$ laser is used to score the gold or tin oxide/gold polyester film (25W laser available from Synrad, Inc., San Diego, Calif.). As illustrated in FIG. 2, the film is scored by the laser creating scoring line 27 and 28 such that two electrodes at sample fluid end 110 and three contact points 122, 123 and 124 were formed at electrical contact end 120. The scoring line is very thin but sufficient to create two separate electrical conductors. An additional scoring line 29 made be made, but is not necessary, along the outer edge of base layer 20 to avoid potential static problems which could cause a noisy signal from the finished sensor 10.

A piece of double-sided tape (Arcare® 7840) available from Adhesive Research, Glen Rock, Pa., is cut to size and shape forming middle layer 30 with U-shaped channel 32 so that it will cover a majority of the conductive layer 21 of base layer 20 except for exposing a small electrical contact area at electrical contact end 120 illustrated in FIG. 1. The U-shaped channel 32 is cut by using the $CO_2$ laser. Middle layer 30 is then layered onto base layer 20. As mentioned earlier, this middle layer 30 serves as a spacer and defines the size of the fluid sample channel 112. It also defines the electrode area 26 which holds the electrode reagent matrix 50. Its width and length is optimized to provide for a relatively quick moving fluid sample. The size of U-shaped channel 32 is about 0.039 in. (1.0 mm) wide by about 0.134 in. (3.4 mm) long. However, the channel width and length can be reduced so that sample volume can be as little as 0.1 microliter.

1.0 microliters of reagent mix is dispensed into channel 32 to form electrodes W, R and $W_0$. The reagent mix is a mixture of a redox mediator, a stabilizer, a binder, a surfactant, a buffer, and an enzyme. The preferred composition for the reagent mix is made by mixing the following percentages of the following ingredients: about 6.5 wt % potassium ferricyanide, about 2.5 wt % polyethylene glycol, about 1 wt % methocel 60 HG, about 0.03 wt % Triton X-100, about 0.05M citrate buffer (pH 5.7), and about 1 wt % glucose oxidase. After the addition of the reagent mix, the device was dried in an oven at 55° C. for about 2 minutes.

After drying, a piece of a transparency film (Cat. No. PP2200 or PP2500 available from 3M) is fashioned into top layer 40. A rectangular vent hole 42 and a semi-circular notch 44 are made using the $CO_2$ laser previously mentioned. The preferred size of vent hole 42 is about 0.039 in. (1.0 mm) by about 0.051 in. (1.30 mm). Vent hole 42 is located approximately 0.087 in. (2.2 mm) from fluid end 110 of sensor 10. Semi-circular notch 44 has a radius of approximately 0.030 in. (0.75 mm) and is recessed from fluid end 110 of sensor 10. Top layer 40 is aligned and layered onto middle layer 30 to complete the assembly of sensor 10, as illustrated in FIG. 1.

Although the description of electrode construction above describes construction for a single sensor, the design and materials used are ideal for making multiple sensors from one piece of each layer material as shown in FIGS. 4A–4C. This is accomplished by starting with a relative large piece of base layer 20 having conducting layer 21 thereon. A plurality of scored lines 27 and 28 are made into conductive layer 21 such that a repetitive pattern, as illustrated in FIG. 4A, is created using the preferred scribing method described previously whereby each pattern will eventually define the three conductive paths 22, 23 and 24 for each sensor. Similarly, a large piece of middle layer 30 having a plurality of elongated cutouts 32 in a repetitive pattern and illustrated in FIG. 4B is layered onto base layer 20. The large piece of middle layer 30 is sized to fit over base layer 20 in such that the plurality of elongated cutouts 32 are aligned over the areas where the scribe lines 27 and 28 intersect exposing three distinct electrode areas W, R and $W_0$, and exposing the plurality of conductive contacts 122, 123 and 124 located at the opposite edge of the strip. The size of each cutout and the amount of reagent mix disposed in each channel 32 are similar to that disclosed above. After dispensing the reagent mix into the respective cutouts, the reagent mix is dried such that each elongated cutout 32 of middle layer 30 contains a thin layer of the reagent matrix. A top layer 40 comparably-sized to and coextensive with middle layer 30 having a plurality of vent openings 42 and notch forming openings 44' in a repetitive pattern, as shown in FIG. 4C, is layered onto middle layer 30. FIG. 4D is a top view of the combined layers. The laminated strip created by the three layers 20, 30 and 40 has a plurality of sensors 10 that can be cut from the laminated strip. The laminated strip is cut longitudinally along line A–A' at fluid sampling end 210 to form a plurality of sampling apertures 114 and longitudinally along line B–B' at electrical contact end 220 to form a plurality of conductive contacts 122,123 and 124. The laminated strip is cut at predetermined intervals along lines C–C' forming a plurality of individual sensors 10. Shaping of the fluid sampling end 120 of each sensor 10, as illustrated in FIG. 1, may be performed if desired. It should be understood by those skilled in the art that the order in which the laminated strip can be cut is not important. For instance, the laminated strip may be cut at the predetermined intervals (C–C') and then the cuts along A–A' and B–B' can be made to complete the process.

A more inclusive description of the wide linear range, the precision and the minimum sample volume features of the present invention along with additional test parameters and examples is provided in U.S. Pat. No. 6,258,229, which is incorporated herein by reference in its entirety.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A disposable electrode strip for testing a fluid sample comprising:
    a laminated strip having a first strip end, a second strip end and a vent opening spaced from said first strip end, said laminated strip comprising a base layer having a conductive layer disposed thereon, said conductive layer having scribe lines delineated thereon and forming three electrode paths, a channel forming layer carried on said base layer, and a cover having an inlet notch at said first strip end;
    an enclosed channel between said first strip end and said vent opening, said enclosed channel sized to hold a volume of said fluid sample less than one microliter;
    a reagent matrix containing at least an enzyme, a stabilizer, wherein said stabilizer is a dissolvable polyalkylene glycol, and a redox mediator disposed on said base layer in said enclosed channel;
    conductive contacts at said second strip end and insulated from said enclosed channel.

2. The electrode strip of claim 1 wherein said enzyme is selected from the group consisting of glucose oxidase, lactate oxidase, cholesterol oxidase, and creatinine amidohydrolase.

3. The electrode strip of claim 1 wherein said redox mediator is at least one metal complex.

4. The electrode strip of claim 3 wherein said redox mediator is potassium ferricyanide or other inorganic or organic redox mediators.

5. The electrode strip of claim 1 wherein said conductive coating is gold.

6. The electrode strip of claim 1 wherein said conductive coating comprising gold and tin oxide.

7. The electrode strip of claim 1 wherein said base layer, said channel forming layer and said cover are made of a plastic dielectric material.

8. The electrode strip of claim 7 wherein said plastic material is selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

9. The electrode strip of claim 1 wherein said enclosed channel is hydrophilic.

10. The electrode strip of claim 1 wherein said enclosed channel has a volume of about 0.2 microliters.

11. The electrode strip of claim 1 wherein said cover has a hydrophilic coating on at least one side.

12. The electrode strip of claim 1 wherein said reagent matrix further contains at least one of a binder, a surfactant, and a buffer.

13. The electrode strip of claim 12 wherein said binder is a cellulose material, and said surfactant is a polyoxyethylene ether.

14. The electrode strip of claim 13 wherein said binder is methyl cellulose, said surfactant is t-octylphenoxypolyethoxyethanol, and said buffer is a citrate buffer.

15. The electrode strip of claim 14 wherein said reagent matrix is made from a mixture having starting components comprising about 1 wt % to about 6.5 wt % of said redox mediator, about 2.5 wt % of said stabilizer, about 1 wt % of said binder, about 0.03 wt % of said surfactant, and about 1 wt % of said enzyme in said citrate buffer.

16. The electrode strip of claim 15 wherein said citrate buffer is about 0.05M.

17. The electrode strip of claim 15 wherein said potassium ferricyanide is 6.5 wt %.

18. The electrode strip of claim 15 wherein said enzyme is glucose oxidase.

19. The electrode strip of claim 1 wherein said channel forming layer has a thickness sufficient to optimize the flow of said fluid sample along said open path.

20. The electrode strip of claim 19 wherein said thickness is about 0.0035 inches (0.089 mm).

21. The electrode strip of claim 1 wherein said enclosed channel contains a working electrode, a pseudo-working electrode and a reference electrode.

22. The electrode strip of claim 21 wherein said pseudo-working electrode is a counter electrode.

23. The electrode strip of claim 21 wherein said pseudo-working electrode is a triggering electrode.

24. The electrode strip of claim 21 wherein said pseudo-working electrode and said reference electrode pair are a resistance-measuring electrode pair.

25. A disposable electrode strip for detecting or measuring the concentration of an analyte in a fluid sample, said electrode strip comprising:
    an insulating base strip having a first base end and a second base end;
    a conductive layer disposed on one side of said base strip, said conductive layer having a pattern scribed into said conductive layer, said pattern delineating three electrically-distinct conductive paths insulated from each other;
    a middle insulator sized smaller thin said insulating base strip and overlaying a substantial portion of said conductive layer, said middle insulator having a cutout portion spaced from said first base end, said cutout portion exposing a limited area of said three conductive paths;
    an electrode material comprising an enzyme, a redox mediator, a stabilizer wherein said stabilizer is a dissolvable polyalkylene glycol, a binder, a surfactant, and a buffer, said electrode material being disposed in said cutout portion; and
    a covering insulator sized to fit over and be coextensive with said middle insulator creating a sample fluid channel, said covering insulator having an inlet notch at a first covering insulator end, said first covering insulator end being coextensive with said first base end, and a covering insulator aperture spaced from said first base end and configured to expose at least a small portion of said cutout portion of said middle insulator.

26. The strip of claim 25 wherein said sample fluid channel has a volume of about 0.22 microliters.

27. The strip of claim 25 wherein said sample fluid channel is hydrophilic.

28. The strip of claim 25 wherein said redox mediator is at least one metal complex selected from the group consisting of ferrocene, ferrocene derivatives and potassium ferricyanide, said binder is a cellulose material, said surfactant is a polyoxyethylene ether, and said buffer has a pH of about 5 to about 6.

29. The strip of claim 28 wherein said mediator is potassium ferricyanide, said binder is methyl cellulose, said surfactant is t-octylphenoxypolyethoxyethanol, and said buffer is a citrate buffer.

30. The strip of claim 29 wherein said electrode material is made of a mixture having starting components comprising about 6.5 wt % of said potassium ferricyanide, about 2.5 wt % of said polyethylene glycol, about 1 wt % of said methyl cellulose, and about 0.03 wt % of said t-octylphenoxypolyethoxyethanol, and about 1 wt % of said enzyme in said citrate buffer.

31. The strip of claim 30 wherein said enzyme is glucose oxidase.

32. The strip of claim 25 wherein said insulating base strip, said middle insulator, and said covering insulator are made from a plastic material selected from the group consisting of polyvinyl chloride, polycarbonate, polysulfone, nylon, polyurethane, cellulose nitrate, cellulose propionate, cellulose acetate, cellulose acetate butyrate, polyester, acrylic, and polystyrene.

33. The electrode strip of claim 25 wherein said sample fluid channel contains a working electrode, a pseudo-working electrode and a reference electrode.

34. The electrode strip of claim 33 wherein said pseudo-working electrode is a counter electrode.

35. The electrode strip of claim 33 wherein said pseudo-working electrode is a triggering electrode.

36. The electrode strip of claim 33 wherein said pseudo-working electrode and said reference electrode pair are a resistance-measuring electrode pair.

37. A laminated biosensor strip comprising:
a base layer with an electrode end and an electrical contact end, said base layer having an electrically conductive coating on one side wherein said conductive coating has a plurality of scribed lines delineating a first conductive path having an L-shape, a second conductive path having a mirror-image L-shape wherein the L-shape ends of said first and second conductive paths are adjacent to each other, and a third conductive path which is shorter than either of said first and second conductive paths, has a linear, elongated shape wherein said L-shaped ends of said first and second conductive paths and the end of said third conductive path are aligned with each other along the central axis of said base layer;
a channel forming layer disposed over said base layer, said channel forming layer having a U-shaped end portion defining a central elongated channel sized to expose a portion of each of said L-shaped ends of said first and second conductive paths and a portion of said third conductive path, said channel forming layer being shorter in length than said base layer wherein a portion of each of said three conductive paths is exposed at said electrical contact end;
a reagent material having at least a redox mediator, a stabilizer, wherein said stabilizer is a dissolvable polyalkylene glycol, and an enzyme disposed within said U-shaped end portion and covering the exposed portions of said first, second and third conductive paths; and
a cover with a vent, said cover disposed on and coextensive with said channel forming layer, said cover, said channel forming layer and said base layer forming a capillary channel with an inlet at one end and communicating with said vent at the other end.

38. The biosensor strip of claim 37 further comprising an inlet notch in said cover.

39. A disposable electrode strip for testing a fluid sample comprising:
a laminated strip having a first strip end, a second strip end and a vent opening spaced from said first strip end, said laminated strip comprising a base layer having a conductive layer disposed thereon, said conductive layer having scribe lines delineated thereon and forming at least two electrode paths, a channel forming layer carried on said base layer, and a cover having an inlet notch at said first strip end;
an enclosed channel between said first strip end and said vent opening, said enclosed channel sized to hold a volume of said fluid sample less than one microliter;
a reagent matrix containing at least an enzyme, a stabilizer, wherein said stabilizer is a dissolvable polyalkylene glycol, and a redox mediator disposed on said base layer in said enclosed channel;
conductive contacts at said second strip end and insulated from said enclosed channel.

40. The biosensor of claim 39 wherein said enzyme is selected from the group consisting of glucose oxidase, lactate oxidase, cholesterol oxidase, and creatinine amidohydrolase.

41. The biosensor of claim 39 wherein said reagent further contains at least one of a binder, a surfactant, and a buffer.

42. The biosensor of claim 41 wherein said binder is a cellulose material and said surfactant is a polyoxyethylene ether.

43. The biosensor of claim 42 wherein said binder is methyl cellulose, said surfactant is t-octylphenoxypolyethoxyethanol, and said buffer is a citrate buffer.

44. The biosensor of claim 41 wherein said reagent is made from a mixture having starting components comprising about 1 wt % to about 6.5 wt % of said redox mediator, about 2.5 wt % of said stabilizer, about 1 wt % of said binder, about 0.03 wt % of said surfactant, and about 1 wt % of said enzyme in said buffer.

45. The biosensor of claim 41 wherein said reagent is made from a mixture having starting components comprising about 6.5 wt % of said redox mediator, about 2.5 wt % of said stabilizer, about 1 wt % of said binder, about 0.03 wt % of said surfactant, about 1 wt % of said enzyme dissolved in a buffered solvent.

46. The biosensor of claim 41 wherein said enzyme is glucose oxidase.

47. The biosensor of claim 41 wherein said reagent is made of a mixture having starting components comprising about 6.5 wt % of potassium ferricyanide, about 2.5 wt % of polyethylene glycol, about 1 wt % of methyl cellulose, about 0.03 wt % t-octylphenoxypolyethoxyethanol, about 1 wt % of said enzyme dissolved in said buffer wherein said buffer is about a 0.05M citrate buffer.

* * * * *